US011555217B2

(12) United States Patent
Daunert et al.

(10) Patent No.: US 11,555,217 B2
(45) Date of Patent: Jan. 17, 2023

(54) KITS AND METHODS FOR PATHOGEN DETECTION

(71) Applicant: UNIVERSITY OF MIAMI, Miami, FL (US)

(72) Inventors: Sylvia Daunert, Miami, FL (US); Sapna K. Deo, Miami, FL (US); Erin Kobetz, Miami, FL (US); David Broyles, Miami, FL (US); Anita Manfredi, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 0 days.

(21) Appl. No.: 16/930,562

(22) Filed: Jul. 16, 2020

(65) Prior Publication Data

US 2020/0340049 A1  Oct. 29, 2020

Related U.S. Application Data

(62) Division of application No. 15/555,273, filed as application No. PCT/US2016/020464 on Mar. 2, 2016, now Pat. No. 10,808,278.

(60) Provisional application No. 62/127,589, filed on Mar. 3, 2015.

(51) Int. Cl.
*C12Q 1/6853* (2018.01)
*C12Q 1/6844* (2018.01)
*C12N 15/09* (2006.01)
*C12Q 1/04* (2006.01)

(52) U.S. Cl.
CPC ........... *C12Q 1/6853* (2013.01); *C12N 15/09* (2013.01); *C12Q 1/04* (2013.01); *C12Q 1/6844* (2013.01); *C12Q 2525/307* (2013.01); *C12Q 2527/101* (2013.01); *C12Q 2531/125* (2013.01); *G01N 2333/025* (2013.01)

(58) Field of Classification Search
CPC ...... C12Q 1/6853; C12Q 1/04; C12Q 1/6844; C12Q 2525/307; C12Q 2527/101; C12Q 2531/125; C12N 15/09; G01N 2333/025
See application file for complete search history.

(56) References Cited

U.S. PATENT DOCUMENTS

| | | | |
|---|---|---|---|
| 5,854,033 A | 12/1998 | Lizardi | |
| 6,221,603 B1 | 4/2001 | Mahtani | |
| 6,911,307 B1 | 6/2005 | Dautel et al. | |
| 2005/0202427 A1 | 9/2005 | Soufla | |
| 2007/0218477 A1 | 9/2007 | Thomas | |
| 2010/0047773 A1* | 2/2010 | Koch | C12Q 1/682 435/6.12 |
| 2014/0349288 A1* | 11/2014 | Church | C12Q 1/6813 435/6.11 |
| 2016/0324506 A1* | 11/2016 | Tariyal | A61B 5/157 |
| 2016/0369321 A1* | 12/2016 | Landegren | C12Q 1/6804 |
| 2017/0335382 A1* | 11/2017 | Bodnar | C12Q 1/6846 |

FOREIGN PATENT DOCUMENTS

| | | | |
|---|---|---|---|
| CN | 102703606 | * | 7/2014 |
| EP | 1586663 A1 | | 10/2005 |
| EP | 1895018 A2 | | 3/2008 |
| EP | 2557156 A1 | | 2/2013 |
| FR | 2786789 A1 | | 6/2000 |

OTHER PUBLICATIONS

Yan et al., Chemical Communications, 50: 7147-7149, (Year: 2014).*
Brown, Dot and Slot blotting of DNA. Curr. Prot. Molec. Biol., Blotting of DNA. Current Protocols in Molecular Biology. 21:IV:2.9B:2.9.15-2.9.20 (2009).
Cartwright et al., Comparison of nucleic acid amplification assays with BD affirm VPIII for diagnosis of vaginitis in symptomatic women. *J. Clin. Biol.*, 51:3694-9 (2013).
Cartwright et al., Development and validation of a semiquantitative, multitarget PCR assay for diagnosis of bacterial vaginosis. *J. Clin. Biol.*, 50:2321-9 (2012).
Emmadi et al., Molecular methods and platforms for infectious diseases testing a review of FDA-approved and cleared assays. *J Mol Diagn* 13:583-604 (2011).
Fredricks et al., Targeted PCR for detection of vaginal bacteria associated with bacterial vaginosis. *J. Clin. Microbiol.* 45:3270-6 (2007).
Gaydos et al., Performance of the Abbott RealTime CT/NG for detection of Chlamydia trachomatis and Neisseria gonorrhoeae. *J. OM. Microbiol.* 48(9):3236-43 (2010).
Kim et al., A rapid and simple isothermal nucleic acid amplification test for detection of herpes simplex virus types 1 and 2. *J. Clin. Virol.*, 50:26-30 (2012).
McGowin et al., Persistent Mycoplasma genitalium infection of human endocervical epithelial cells elicits chronic inflammatory cytokine secretion. *Infect. Immun.*, 80:3842-3849 (2012).
Muller et al., Development of a rotor-gene real-time PCR assay for the detection and quantification of Mycoplasma genitalium. *J. Microbiol. Meth.*, 88:311-5 (2012).
Nilsson et al., Padlock probes: circularizing oligonucleotides for localized DNA detection. *Science*, 265(5181):2085-8 (1994).

(Continued)

*Primary Examiner* — Cynthia B Wilder

(74) *Attorney, Agent, or Firm* — Marshall, Gerstein & Borun LLP

(57) ABSTRACT

Kits and methods for detecting pathogens without the need for laboratory equipment are disclosed. The kits and methods described herein allow for near-room temperature amplification of pathogen polynucleotides in a biological sample in a one-compartment reaction vessel. The kits and methods may be used to detect any target nucleic acid, such as DNA or RNA from a bacterial, fungal, or viral pathogen.

18 Claims, 2 Drawing Sheets

Specification includes a Sequence Listing.

(56) References Cited

OTHER PUBLICATIONS

Papp et al., Recommendations for the Laboratory-Based Detection of Chlamydia trachomatis and Neisseria gonorrhoeae. Centers for Disease Control and Prevention Recommendations and Reports, 63P:1-19 (2014).
Van Der Pol et al., Type-specific identification of anogenital herpes simplex virus infections by use of a commercially available nucleic acid amplification test. *J. Clin. Microbiol* 50: 3466-3471 (2012).
International Search Report and Written Opinion of the International Search Authority, PCT/US2016/020464, dated Jun. 3, 2016.
International Preliminary Reporton Patentability, PCT/US2016/020464, dated Sep. 5, 2017.
Andrea et al., Comparison of Aptima Trichomonas vaginalis transcription-mediated amplification assay and BD affirm VPIII for detection of T. vaginalis in symptomatic women: performance parameters and epidemiological implications. *J. Clin. Microbiol.*, 49(3):866-9 (2011).
Yan et al., Convenient detection of HPV virus in a clinical sample using concurrent rolling circle and junction probe amplifications, *Chemical Communications*. 50:7147-7149 (2014).
Mothershed et al., Nucleic acid-based methods for the detection of bacterial pathogens: present and future considerations for the clinical laboratory, *Clinica Chimica Acta*. 363:206-20 (2006).
Genbank Accession No. AXX04780, Human papillomavirus type 16 E6 gene specific PCR primer, SEQ ID No. 4, May 13, 2010.
Genbank Accession No. AZS79472, Human let7d padlock probe, SEQ ID No. 13, Mar. 15, 2012.
Extended European Search Report, PCT/US2016/020464 (Aug. 1, 2018).

\* cited by examiner

SEQUENCE LISTING

```
<160> NUMBER OF SEQ ID NOS: 21

<210> SEQ ID NO 1
<211> LENGTH: 24
<212> TYPE: DNA
<213> ORGANISM: Human papillomavirus

<400> SEQUENCE: 1
tgcaccaaaa gagaactgca atgt                                            24

<210> SEQ ID NO 2
<211> LENGTH: 75
<212> TYPE: DNA
<213> ORGANISM: Artificial Sequence
<220> FEATURE:
<223> OTHER INFORMATION: Synthetic probe

<400> SEQUENCE: 2
tcttttggtg catttatttc ctcaatgctg ctgctgtact actagtgatt tacttggatg      60
tctacattgc agttc                                                      75

<210> SEQ ID NO 3
<211> LENGTH: 12
<212> TYPE: DNA
<213> ORGANISM: Artificial Sequence
<220> FEATURE:
<223> OTHER INFORMATION: Synthetic probe

<400> SEQUENCE: 3
tcttttggtg ca                                                         12

<210> SEQ ID NO 4
<211> LENGTH: 12
<212> TYPE: DNA
<213> ORGANISM: Artificial Sequence
<220> FEATURE:
<223> OTHER INFORMATION: Synthetic probe

<400> SEQUENCE: 4
acattgcagt tc                                                         12

<210> SEQ ID NO 5
<211> LENGTH: 26
<212> TYPE: DNA
<213> ORGANISM: Artificial Sequence
<220> FEATURE:
<223> OTHER INFORMATION: Synthetic probe
```

-continued

<400> SEQUENCE: 5
tttatttcct caatgctgct gctgta                                      26

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
agcagcagca ttgaggaaat                                             20

<210> SEQ ID NO 7
<211> LENGTH: 19
<212> TYPE: DNA
<213> ORGANISM: Chlamydia trachomatis

<400> SEQUENCE: 7
acgattgttt agtggcgga                                              19

<210> SEQ ID NO 8
<211> LENGTH: 71
<212> TYPE: DNA
<213> ORGANISM: Artificial Sequence
<220> FEATURE:
<223> OTHER INFORMATION: Synthetic probe

<400> SEQUENCE: 8
aacaatcgtt ttatttcctc aatgctgctg ctgtactact agtgatttac ttgggatgtc    60
ttccgccact a                                                       71

<210> SEQ ID NO 9
<211> LENGTH: 9
<212> TYPE: DNA
<213> ORGANISM: Artificial Sequence
<220> FEATURE:
<223> OTHER INFORMATION: Synthetic probe

<400> SEQUENCE: 9 aacaatcgt                                                          9

<210> SEQ ID NO 10
<211> LENGTH: 10
<212> TYPE: DNA
<213> ORGANISM: Artificial Sequence
<220> FEATURE:
<223> OTHER INFORMATION: Synthetic probe

<400> SEQUENCE: 10
tccgccacta                                                         10

<210> SEQ ID NO 11
<211> LENGTH: 26
<212> TYPE: DNA
<213> ORGANISM: Artificial Sequence
<220> FEATURE:
<223> OTHER INFORMATION: Synthetic probe

<400> SEQUENCE: 11
tttatttcct caatgctgct gctgta                                      26

<210> SEQ ID NO 12

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
agcagcagca ttgaggaaat                                               20

<210> SEQ ID NO 13
<211> LENGTH: 20
<212> TYPE: DNA
<213> ORGANISM: Neisseria gonorrhoeae

<400> SEQUENCE: 13
actgcgttct gaactgggtg                                               20

<210> SEQ ID NO 14
<211> LENGTH: 71
<212> TYPE: DNA
<213> ORGANISM: Artificial Sequence
<220> FEATURE:
<223> OTHER INFORMATION: Synthetic probe

<400> SEQUENCE: 14
agaacgcagt tttatttcct caatgctgct gctgtactac tagtgattta cttggatgtc   60
tcacccagtt c                                                        71

<210> SEQ ID NO 15
<211> LENGTH: 10
<212> TYPE: DNA
<213> ORGANISM: Artificial Sequence
<220> FEATURE:
<223> OTHER INFORMATION: Synthetic probe

<400> SEQUENCE: 15
agaacgcagt                                                          10

<210> SEQ ID NO 16
<211> LENGTH: 10
<212> TYPE: DNA
<213> ORGANISM: Artificial Sequence
<220> FEATURE:
<223> OTHER INFORMATION: Synthetic probe

<400> SEQUENCE: 16
cacccagttc                                                          10

<210> SEQ ID NO 17
<211> LENGTH: 26
<212> TYPE: DNA
<213> ORGANISM: Artificial Sequence
<220> FEATURE:
<223> OTHER INFORMATION: Synthetic probe

<400> SEQUENCE: 17
tttatttcct caatgctgct gctgta                                        26

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
```

```
agcagcagca ttgaggaaat                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19
tgctgccggt cacttaacat                                               20

<210> SEQ ID NO 20
<211> LENGTH: 85
<212> TYPE: DNA
<213> ORGANISM: Artificial Sequence
<220> FEATURE:
<223> OTHER INFORMATION: Synthetic primer

<400> SEQUENCE: 20
catctgaaaa aatttttatg ttaagtgacc ggcagcattt tttctaatct gaagcttggt   60
ggactctttt tttcactagg cagcc                                         85

<210> SEQ ID NO 21
<211> LENGTH: 7
<212> TYPE: DNA
<213> ORGANISM: Artificial Sequence
<220> FEATURE:
<223> OTHER INFORMATION: Synthetic probe

<400> SEQUENCE: 21 aaagaga                                                              7
```

KITS AND METHODS FOR PATHOGEN DETECTION

CROSS-REFERENCE TO RELATED APPLICATION

The application is a divisional of U.S. patent application Ser. No. 15/555,273, filed Sep. 1, 2017, which is a national phase of International Patent Application No. PCT/US16/20464, filed Mar. 2, 2016, and which claims benefit under 35 U.S.C. § 119(e) of U.S. Provisional Patent Application No. 62/127,589, filed Mar. 3, 2015, are hereby claimed, and the disclosures thereof are incorporated herein by reference.

FIELD OF THE INVENTION

The disclosure relates to test kits and methods for detecting pathogens in biological samples.

INCORPORATION BY REFERENCE

This application contains, as a separate part of the disclosure, a sequence listing in computer-readable form (filename: 49096B_SeqListing.txt, 4,485 bytes, created Jul. 16, 2020), which is incorporated by reference in its entirety.

BACKGROUND

Advances in technology relating to pathogen detection in biological specimens have been instrumental in the successful management of many infectious diseases. Several laboratory tests for the diagnosis of diseases such as human papillomavirus (HPV), *chlamydia* and gonorrhea are commercially available. The majority of the tests currently on the market are based on the polymerase chain reaction (PCR), with a few that rely on fluorescence immunoassay. These tests are extremely sensitive and accurate, but cannot be performed outside clinical settings. Diagnostic tests based on PCR and/or immunoassays require expensive laboratory equipment and are usually adapted for automation by large, well-equipped facilities staffed by highly-trained personnel. These tests are costly and may take weeks to process, creating significant hurdles for routine screening. Furthermore, the laboratory infrastructure and instrumentation required to run these assays are not universally available, limiting their dissemination. As a result, individuals without routine access to a formal healthcare system are at increased risk of developing and dying from preventable diseases.

To increase screening rates, especially among disadvantaged populations, self-sampling techniques have been developed. For example, self-collected vaginal swabs are the currently preferred specimen types for *chlamydia* and gonorrhea testing. Self-collected samples are mailed to diagnostics laboratories for testing. Thus, it still takes weeks to obtain the results, and the reliance on expensive (and sometimes scarce) resources is not significantly reduced.

There exists a need for testing platforms and methods that are simple to use, provide rapid results, and eliminate the need for laboratory equipment. Such cost-effective, portable tests and methods would provide means for the detection and early treatment of pathogenic infections beyond what is currently available.

SUMMARY

The disclosure is directed to test kits and methods for detecting pathogens in biological samples that do not require laboratory instrumentation. In one aspect, a method for detecting a pathogen polynucleotide in a biological sample comprising an amplification step and a detection step is provided. The amplification step comprises combining the biological sample with (a) a padlock probe comprising a 5' end complementary to a first section of the pathogen polynucleotide and a 3' end complementary to a second section of the pathogen polynucleotide, wherein the first section and second section of the pathogen polynucleotide sequences are located adjacent to each other; (b) a ligase; (c) a primer comprising a polynucleotide sequence complementary to a portion of the padlock probe; (d) a polymerase; (e) a reporter probe; and (f) a reaction buffer; to form a mixture in a single reaction vessel. The detection step comprises wicking the mixture into a test strip and visually detecting the reporter probe on the test strip. Optionally, the amplification step does not comprise incubating the mixture at a temperature greater than about 37° C. Optionally, the amplification step comprises incubating the mixture at a temperature between about 20° C. and about 37° C., for example, about 30° C., for about 20 minutes to about 2 hours.

In another aspect, the invention provides a kit for detecting a pathogen polynucleotide in a biological sample, comprising (a) a reaction vessel comprising: (1) a padlock probe comprising a 5' end complementary to a first section of the pathogen polynucleotide and a 3' end complementary to a second section of the pathogen polynucleotide, wherein the first section and second section of the pathogen polynucleotide sequence are located adjacent to each other; (2) a ligase; (3) a primer comprising a polynucleotide complementary to a portion of the padlock probe; (4) a polymerase; and (5) a reporter probe; (b) a reaction buffer that supports polynucleotide ligation and polymerization; and (c) a test strip. In various embodiments, the reaction buffer is included in the reaction vessel.

In various aspects, the pathogen is selected from the group consisting of human papillomavirus, *Chlamydia tracomatis*, *Neisseria gonorrhoeae*, herpes simplex virus (Type 1 or Type 2), *Mycoplasma genitalium, Trichomonas vaginalis, Gardnerella vaginalis*, and *Candida* species. In one aspect, the ligase is T4 DNA ligase. In another aspect, the polymerase is (1)29 polymerase or Bst DNA polymerase. Combinations of polymerases may also be used. In still another aspect, the reaction buffer comprises Tris-Cl, magnesium chloride, ammonium sulfate, ATP, and optionally methanol. The reaction buffer optionally comprises about 50 mM to about 1 mM Tris-Cl, about 10 mM to about 100 mM magnesium chloride, about 5 mM to about 100 mM ammonium sulfate, about 0.1 mM to about 10 mM ATP, and about 0% to about 20% methanol.

In various aspects, the padlock probe comprises a polynucleotide sequence selected from the group consisting of SEQ ID NO:2, SEQ ID NO:3, SEQ ID NO:4, SEQ ID NO:8, SEQ ID NO:9, SEQ ID NO:10, SEQ ID NO:14, SEQ ID NO:15, and SEQ ID NO:16; the primer comprises a polynucleotide sequence selected from the group consisting of SEQ ID NO:6, SEQ ID NO:12, and SEQ ID NO:18; and/or the reporter probe comprises a polynucleotide sequence (a) selected from the group consisting of SEQ ID NO: 5, SEQ ID NO:11 and SEQ ID NO: 17 or (b) corresponding to a region of SEQ ID NO: 2, SEQ ID NO:8 or SEQ ID NO: 14. All combinations of padlock probes, primers, and reporter probes described herein are contemplated, as are use of probes and primers comprising sequences having at least about 90% identity to SEQ ID NOS: 2-21.

Optionally, the reporter probe is conjugated to a microparticle, for example, a microparticle having a diameter less than about one micrometer. In various aspects, the microparticle is a nylon microparticle, a gold microparticle, or a magnetic microparticle. In one aspect, the test strip comprises filter paper, optionally filter paper having a pore size of about 11 micrometers. Optionally, the test strip comprises chitosan.

In one aspect, the pathogen is HPV; the padlock probe comprises a polynucleotide sequence selected from the group consisting of SEQ ID NO:2, SEQ ID NO:3, SEQ ID NO:4, and SEQ ID NO:20; the primer comprises the polynucleotide sequence of SEQ ID NO: 6, SEQ ID NO:19, or SEQ ID NO:21; and the reporter probe comprises the polynucleotide sequence of SEQ ID NO: 5 or a polynucleotide corresponding to a region of SEQ ID NO:2. In another aspect, the pathogen is *Chlamydia tracomatis*; the padlock probe comprises a polynucleotide sequence selected from the group consisting of SEQ ID NO:8, SEQ ID NO:9, and SEQ ID NO:10; the primer comprises the polynucleotide sequence of SEQ ID NO: 12, and the reporter probe comprises the polynucleotide sequence of SEQ ID NO: 11 or a polynucleotide corresponding to a region of SEQ ID NO:8. In still another aspect, the pathogen is *Neisseria gonorrhoeae*, the padlock probe comprises a polynucleotide sequence selected from the group consisting of SEQ ID NO:14, SEQ ID NO:15, and SEQ ID NO:16; the primer comprises the polynucleotide sequence of SEQ ID NO:18, and the reporter probe comprises the polynucleotide sequence of SEQ ID NO:17 or a polynucleotide corresponding to a region of SEQ ID NO:14. Probes and primers comprising sequences having at least about 90% identity to any of the sequences referenced herein also are contemplated.

The foregoing summary is not intended to define every aspect of the invention, and other features and advantages of the present disclosure will become apparent from the following detailed description, including the drawings. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the invention narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure.

BRIEF DESCRIPTION OF THE FIGURES

FIG. 2A depicts a negative result with no signal below the control band (arrow), indicating the pathogen polynucleotide is not present in the biological sample, and FIG. 2B depicts a positive result (asterisk) below the control band (arrow), indicating a pathogen polynucleotide is present in the biological sample.

DETAILED DESCRIPTION

The present disclosure provides kits and methods for detecting pathogens in biological samples that eliminate the need for laboratory equipment. The kits and methods provide a solution to diagnosing infection and managing public health in medically underserved populations worldwide, while specifically addressing health challenges faced by developing communities.

Figure 1:
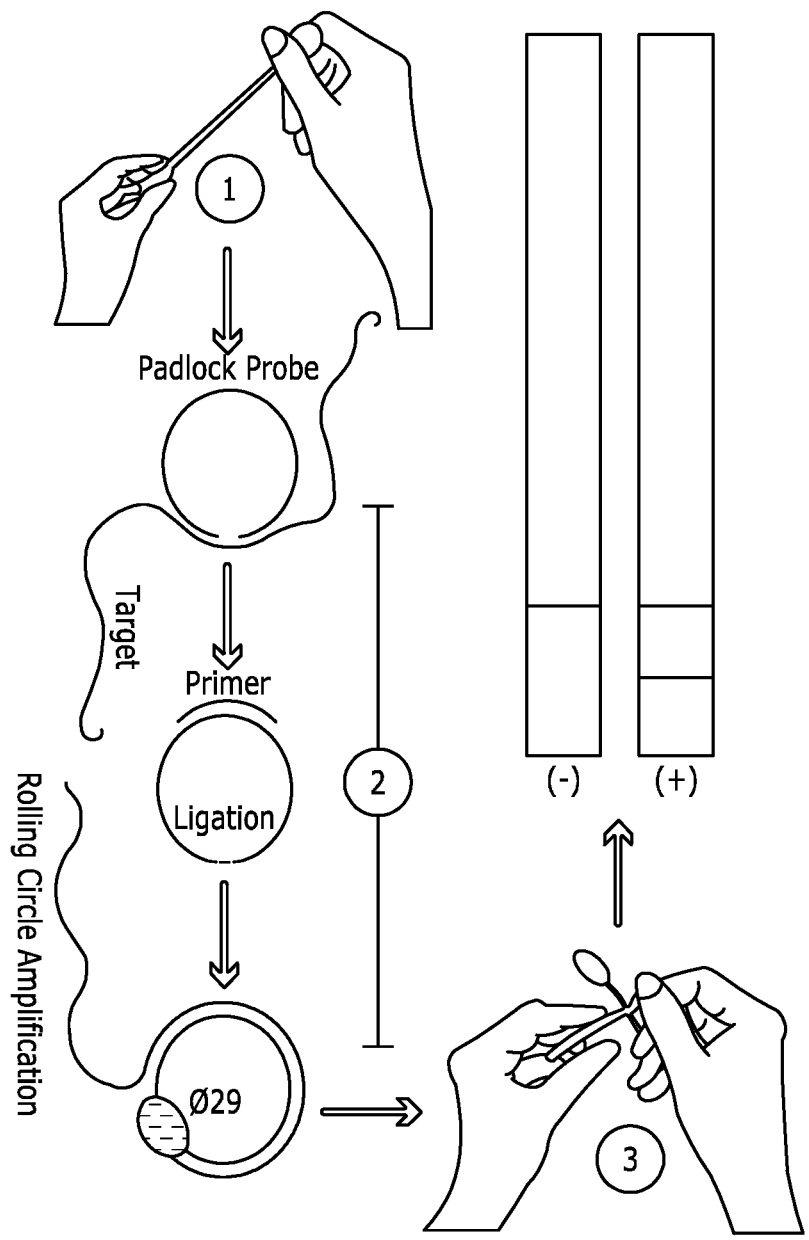
FIG. 1 depicts a schematic of a method of the disclosure. First, a swab containing a biological sample is transferred to a reaction tube containing polynucleotide amplification reagents as well as reporter probe. Second, the mixture in the reaction tube is incubated, optionally in the hand. The padlock probe hybridizes to target pathogen polynucleotides via a 5' complementary end and a 3' complementary end. Ligation occurs, forming a circular padlock probe, to which a primer anneals. Rolling circle amplification (RCA) occurs, generating antisense copies of the padlock probe. The reporter probe comprises a polynucleotide sequence complementary to the newly generated antisense copies of the padlock probe and hybridizes to the RCA product. Third, a test strip is inserted in the reaction tube. The mixture in the reaction tube is wicked through the test strip and a positive or negative result is visualized.

The kits and methods of the disclosure provide numerous advantages compared to currently marketed tests. The kits and methods of the disclosure use isothermal rolling-circle amplification (RCA) in order to eliminate reverse transcription and allow for near-room temperature amplification of polynucleotides in a one-compartment reaction vessel, allowing for on-site detection of target pathogen polynucleotides without requiring expensive instrumentation, technical training, or complex protocols (FIG. 1). Therefore, unlike other methods for pathogen detection, the kits and methods of the disclosure do not require any laboratory equipment such as PCR machines or separation columns.

Additionally, the polynucleotide amplification reactions can be run at constant temperatures (e.g., staying within five degrees from the starting temperature) that are near ambient or room temperature, for example, about 20° C. to about 37° C. The reactions can thus be performed using, for example, body heat such as the heat from one's hand, rather than requiring temperature cycling for different steps of the reaction and/or heated water baths or incubators.

The reactions can be run in a single reaction vessel, using a multi-functional buffer that supports both polynucleotide ligation and polymerization reactions, eliminating the need for sequential process steps requiring the addition of reagents in series, or multiple separate reaction compartments. The test strip serves as a separation device that detects reporter probes hybridized to amplified target nucleic acids based on size exclusion, eliminating the need for capture probes embedded in the test strip. Because the amplification can be completed in as little as 20-30 minutes, virtually immediate results can be provided on-site, rather than requiring days or weeks for results to be returned from a clinician or laboratory. After the tests are completed, the reaction vessel and test strips can be easily disposed of without risk of contamination because the RCA products are non-replicating, unlike amplicons produced using PCR or other methods.

The kits and methods of the disclosure thus overcome many cultural, geographic, and economic barriers that currently preclude adequate disease screening. Use of the kits and methods of the present disclosure as a primary screening strategy improves disease prevention and treatment. Rapid testing eliminates the need for follow-up consultations and allows immediate treatment, when necessary. The kits and methods of the disclosure are useful for rapid on-site disease detection in doctor's offices, point of care facilities, community clinics, pharmacies, hospitals, ambulances and other first responder vehicles (e.g., firetrucks, helicopters, airplanes, etc.), and at home. The kits and methods are also useful in preventing and monitoring food- and water-borne illnesses due to contamination by pathogens.

The kits and methods of the disclosure are applicable to DNA and RNA, whether single-stranded or double-stranded. Any bacterial, fungal, or viral pathogen may be detected using the kits and methods of the disclosure. For example, in one aspect, the kits and methods are used to detect a bacterial pathogen including, but not limited to, bacteria belonging to the genus *Bacillus* (e.g., *B. anthracis*), *Bordetella* (e.g. *B. pertussis*), *Borrelia* (e.g., *B. burgdorferi*), *Brucella* (e.g., *B. abortus, B. canis, B. melitensis, B. suis*), *Campylobacter* (e.g., *C. jejuni*), *Chlamydia* (e.g., *C. pneumonia, C. psittaci, C. trachomatis*), *Clostridium* (e.g., *C. botulinum, C. difficile, C. perfringens*), *Corynebacterium* (e.g., *C. diphtheria*), *Enterococcus* (e.g., *E. faecalis*), *Escheria* (e.g., *E. coli*), *Gardnerella* (e.g., *G. vaginalis*), *Haemophilus*, (e.g., *H. influenza*), *Helicobacter* (e.g., *H. pylori*), *Legionea* (e.g., *L. pneumophila*), *Listeria*, (e.g., *L. monocytogenes*), *Mycoplasma* (e.g., *M. genitalium*), *Neisseria* (e.g., *N. gonorrhoeae, N. meningitides*), *Pseudomonas* (e.g., *P. aeruginosa*), *Salmonella* (e.g., *S. typhi, S. typhimurium*), *Staphylococcus* (e.g., *S. aureus*), *Streptococcus* (e.g, *S. pneumonia*), or *Vibrio* (e.g., *V. cholerae*). In another aspect, the kits and methods are used to detect a fungal pathogen including, but not limited to, fungi belonging to the genus *Aspergillus, Blastomyces, Candida, Cladosporium, Coccidioides, Cryptococcus, Exserohilum, Histoplasma, Mucoromycotina, Pneumocystis, Sporothrix,* or *Stachybotrys*. In still another aspect, the kits and methods are used to detect a viral pathogen including, but not limited to, adeno-associated virus, dengue virus, Ebolavirus, encephalomyocarditis virus, Epstein-Barr virus, hepatitis virus, herpesvirus (e.g., herpes simplex virus Type 1 or Type 2), human immunodeficiency virus (HIV), HPV, influenza virus, MERS coronavirus, measles virus, mumps virus, Norovirus, poliovirus, rotavirus, rubella virus, West Nile virus, and yellow fever virus, or a protozoan pathogen including, but not limited to, *Trichomonas vaginalis*. The genomes of the representative pathogens referenced above are known in the art, and generation of a padlock probe with complementary sequences suitable for hybridization is well within the skill of the art. In one aspect, the pathogen polynucleotide comprises a target polynucleotide selected from the genome of HPV, *Chlamydia tracomatis*, or *Neisseria gonorrhoeae*, such as the polynucleotide of SEQ ID NO: 1, SEQ ID NO:7, or SEQ ID NO:13.

The following definitions may be useful in aiding the skilled practitioner in understanding the disclosure. Unless otherwise defined herein, scientific and technical terms used in the present disclosure shall have the meanings that are commonly understood by those of ordinary skill in the art.

The term "capture region" refers to a region on a conventional test strip containing immobilized capture probes which bind to a target polynucleotide and allow for visual detection of the target polynucleotide.

The term "constant temperature" refers to temperatures that are within ±5° C. of a reference temperature.

The term "microparticle" refers to a particle comprising a diameter less than 100 micrometers and includes particles having a diameter less than one micrometer. Microparticles may be spherical (e.g., microbeads) or have an irregular shape, and may be composed of any of a number of substances, including gold and/or other metals, nylon and/or other polymers, magnetic compounds, and combinations thereof.

The term "padlock probe" refers to a single-stranded polynucleotide whose 5' and 3' ends are complementary to a target polynucleotide sequence, for example, as described in Nilsson et al., Science 265(5181):2085-2088 (1994), incorporated herein by reference.

The term "primer" refers to a polynucleotide that hybridizes to a target polynucleotide sequence and serves as the starting point for synthesis of new polynucleotides.

The term "rolling circle amplification" or "RCA" refers to the isothermal amplification of a circularized probe, for example, as described in U.S. Pat. No. 5,854,033, incorporated herein by reference.

In one aspect, the disclosure provides a method for detecting a pathogen polynucleotide in a biological sample comprising an amplification step comprising combining the biological sample with (1) a padlock probe comprising a 5' end complementary to a first section of the pathogen polynucleotide and a 3' end complementary to a second section of the pathogen polynucleotide, wherein the first section and the second section of the pathogen polynucleotide are adjacent to each other; (2) a ligase; (3) a primer comprising a polynucleotide sequence complementary to a portion of the padlock probe; (4) a polymerase; (5) a reporter probe; and (6) a reaction buffer. A detection step is then performed.

In another aspect, the disclosure provides a test kit for detection of a pathogen polynucleotide in a biological sample comprising a reaction vessel comprising: (1) a padlock probe comprising a 5' end complementary to a first section of the pathogen polynucleotide sequence and a 3' end complementary to a second section of the pathogen polynucleotide sequence, wherein the first section and second section of pathogen polynucleotide sequences are located adjacent to each other; (2) a ligase that anneals the 5' and 3' ends of the padlock probe to form a circular padlock probe; (3) a primer comprising a polynucleotide sequence complementary to a portion of the padlock probe; (4) a polymerase; and (5) a reporter probe. The kit further comprises a reaction buffer that supports polynucleotide ligation and polymerization and a test strip for detecting the reporter probe.

The biological sample is, in various embodiments, obtained from a human or other mammalian subject, for example, by collecting a bodily fluid sample or swabbing a body orifice. The sample may be collected by, e.g., a health care work or self-sampling. Alternatively, the biological sample is obtained from an environmental source, such as a water or soil. The biological sample may also be a food sample (e.g., a fluid or swab taken from food in order to, for example, detect contamination). The biological sample and reagents (padlock probe, ligase, primer, polymerase, reporter probe, and reaction buffer) are combined to form a mixture in a single reaction vessel, such as a test tube.

When the mixture of the biological sample and reagents is formed, if the target pathogen polynucleotide is present in the biological sample, the 5' end and 3' end of the padlock probe hybridize to adjacent first and second sections of the pathogen polynucleotide sequence. In various aspects, the padlock probe comprises a polynucleotide sequence selected from the group consisting of SEQ ID NO:2, SEQ ID NO:3, SEQ ID NO:4, SEQ ID NO:8, SEQ ID NO:9, SEQ ID NO:10, SEQ ID NO:14, SEQ ID NO:15, SEQ ID NO:16, and SEQ ID NO:20. In one aspect, the padlock probe comprises a 5' section comprising the sequence in SEQ ID NO:3, SEQ ID NO:9, or SEQ ID NO:15 and/or a 3' section comprising the sequence set forth in SEQ ID NO:4, SEQ ID NO:10, or SEQ ID NO:16. In another aspect, the padlock probe comprises the polynucleotide sequences of SEQ ID NO:3 and SEQ ID NO:4, SEQ ID NO:9 and SEQ ID NO:10, or SEQ ID NO:15 and SEQ ID NO:16. In still another aspect, the padlock probe comprises the polynucleotide sequence of SEQ ID NO:2, SEQ ID NO: 8, SEQ ID NO:14, or SEQ ID NO:20. Variants comprising a nucleic acid sequence comprising at least about 80%, at least about 90%, or at least about 95% sequence identity to the sequences referenced above also may be used in the context of the invention.

The hybridization of the padlock probe to the pathogen polynucleotide brings the 5' end and 3' end of the padlock probe in close proximity, allowing the ligase to join the 5' end and 3' end of the padlock probe together to form a circular padlock probe. It will be appreciated that the sequences above are merely examples of sequences suitable for use in a padlock probe, and other sequences are suitable for use so long as the sequences hybridize to the target polynucleotide in such a manner to allow a ligase to generate a circular padlock probe. In one aspect, the ligase is an enzyme that can ligate polynucleotide strands at a temperature at or below 37° C., for example T4 DNA ligase. The target pathogen polynucleotide is only briefly required to serve as a bridge to circularize the padlock probe for subsequent amplification.

Once the ligase has circularized the padlock probe, the primer, which comprises a polynucleotide sequence complementary to a portion of the padlock probe, hybridizes to the circular padlock probe to initiate replication of a single-stranded polynucleotide sequence containing repetitive, antisense copies of the padlock probe. In various aspects, the primer comprises a polynucleotide sequence set forth in SEQ ID NO:6, SEQ ID NO:11, SEQ ID NO:17, SEQ ID NO:19 or SEQ ID NO:21, or a polynucleotide sequence complementary to a portion of SEQ ID NO:2, SEQ ID NO:8, SEQ ID NO:14 or SEQ ID:20. Primers comprising a sequence at least 90% identical to these sequences also may be used in various embodiments. The replication of single-stranded antisense copies of the padlock probe is mediated by the polymerase. In one aspect, the polymerase is capable of working on small circular polynucleotides, for example, a polymerase derived from a bacteriophage or bacterium, such as phi29 (129) polymerase or *Bacillus stearothermophilus* (Bst) DNA polymerase (e.g., Bst DNA polymerase, large fragment).

The reporter probe hybridizes to the antisense copies of the padlock probe to form a reporter complex. In one aspect, the reporter probe comprises a polynucleotide sequence identical to a region of the padlock probe, such as the region adjacent to the 5' end of the padlock probe that is complementary to the pathogen polynucleotide. Optionally, the reporter probe comprises a polynucleotide sequence identical to a region of at least 10 polynucleotides of the padlock probe, for example, at least 10 polynucleotides, at least 15 polynucleotides, at least 20 polynucleotides, at least 25 polynucleotides, or at least 30 polynucleotides. In various aspects, the reporter probe comprises a polynucleotide corresponding to a portion of SEQ ID NO:2, SEQ ID NO:8, SEQ ID NO:14, or SEQ ID NO:20, for example, in some embodiments, the reporter probe comprises the polynucleotide sequence of SEQ ID NO:5, SEQ ID NO:11, or SEQ ID NO:17. Other suitable reporter probes may be generated using routine laboratory methods.

Optionally, the reporter probe is conjugated to a microparticle. In one aspect, the microparticle has a diameter less than about one micrometer. In various aspects, the microparticle is selected from a nylon microparticle, gold microparticle, or magnetic (e.g., paramagnetic) microparticle. Combinations of microparticles may also be used. Conjugation of the reporter probe and microparticle can be achieved using any suitable method, such as covalent linkage.

The reaction buffer of the disclosure is capable of supporting both the polynucleotide ligation and polymerization reactions, thereby eliminating the need for more than one buffer, a washing step, or multiple reaction compartments. In one aspect, the reaction buffer comprises Tris-Cl, magnesium chloride, ammonium sulfate, ATP, and optionally methanol, optionally about 10 mM to about 100 mM Tris-Cl, about 2 mM to about 10 mM magnesium chloride, about 1 mM to about 10 mM ammonium sulfate, about 0.1 mM to about 1 mM ATP, pH of about 7.0 to about 7.6, optionally in about 20% v/v methanol. For example, in one aspect, a 10× reaction buffer comprises about 500 mM to about 1 M Tris-HCl, about 100 mM magnesium chloride, and about 50 mM to about 100 mM ammonium sulfate, pH about 7.5 at 25° C., optionally further comprising about 40 mM DTT and/or about 1 mM ATP. In one aspect, the amplification step is performed at a temperature less than about 37° C., unlike traditional PCR reactions, which require laboratory equipment to achieve temperatures greater than 90° C. Therefore, in one aspect, the amplification step does not comprise incubating the mixture at a temperature greater than about 37° C. In one aspect, the amplification step comprises incubating the mixture at a temperature between about 20° C. and about 37° C., for example, between about 22° C. and about 35° C., between about 23° C. and about 32° C., or between about 25° C. and about 30° C. In another aspect, the amplification step does not comprise incubating the mixture at a temperature greater than about 30° C. Optionally, the amplification step comprises incubating the mixture at a constant temperature of about 30° C. The amplification reaction can, therefore, be performed using only body heat, for example, by holding the reaction vessel in the palm of one's hand. In one aspect, the amplification step comprises incubating the mixture at a temperature less than 37° C. for a time of about 20 minutes to about 2 hours, for example, about 20 minutes, about 30 minutes, about 40 minutes, about 50 minutes, about 60 minutes, about 90 minutes or about 2 hours.

Figure 2A:
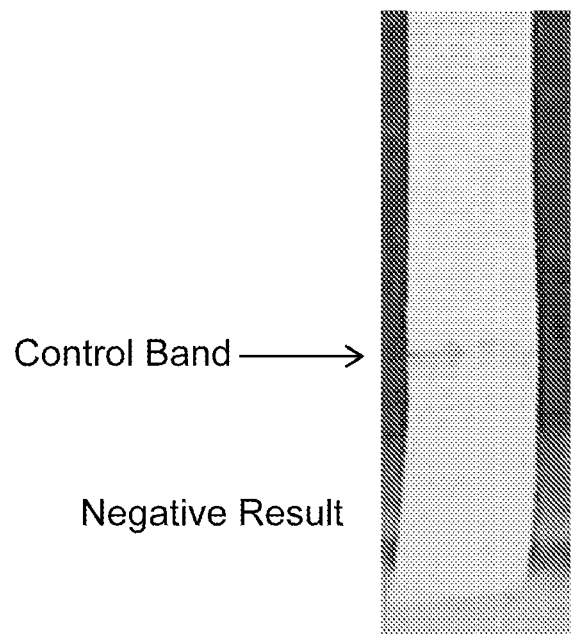
FIG. 2A and FIG. 2B depict representative test strip results of a completed assay.
Figure 2B:
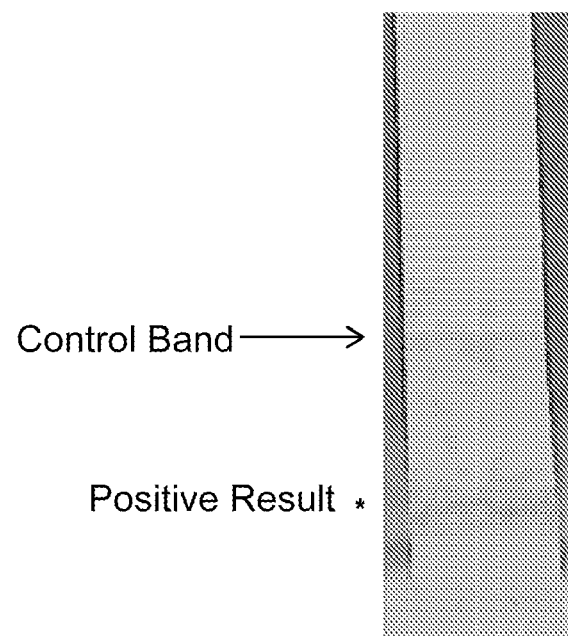

In one aspect, a method of the disclosure further comprises a detection step comprising wicking the mixture, e.g., via capillary action, into a test strip and visually detecting the reporter probe. In one aspect of the kits and methods described herein, the test strip is a paper strip, optionally comprising filter paper, such as Whatman #1 filter paper. The test strip optionally comprises pores having a diameter of about 5 micrometers to about 20 micrometers, for example, about 5 micrometers, about 10 micrometers, about 11 micrometers, about 12 micrometers, about 13 micrometers, about 14 micrometers, about 15 micrometers, or about 20 micrometers. Optionally, the test strip comprises a region comprising chitosan, which non-specifically binds polynucleotides and provides a control region or indicator of test completion. The test strip separates the components in the mixture based on size exclusion so that reporter probes hybridized to amplified polynucleotides, i.e., the reporter complexes, travel less along the length of the test strip than smaller, uncomplexed reporter probes. Thus, when the target pathogen polynucleotide is present in the biological sample, resulting in the production of antisense copies of the padlock probe that hybridize to the reporter probe, a distinct band is visible near the bottom of the test strip, e.g., below an indicator of test completion (FIG. 2B), indicating pathogen polynucleotide is present in the biological sample. In contrast, a test strip dipped into a mixture containing only uncomplexed reporter probes exhibits a band farther up the test strip, e.g., at the mid-point of the strip or at an indicator of test completion, indicating the target pathogen polynucleotide is not present in the biological sample (FIG. 2A). Because the test strip separates the mixture based on size exclusion, no capture region or capture probes embedded in the test strip are required.

In one aspect of the kits and methods of the disclosure, the pathogen is HPV; the padlock probe comprises a polynucleotide sequence selected from the group consisting of SEQ ID NO: 2, SEQ ID NO:3, SEQ ID NO:4, and SEQ ID NO:20; the primer comprises the polynucleotide sequence of SEQ ID NO:6, SEQ ID NO:19, or SEQ ID NO:21; and the reporter probe comprises the polynucleotide sequence of SEQ ID NO:5 or a polynucleotide corresponding to a region of SEQ ID NO:2 or SEQ ID NO:20. In another aspect, the pathogen is *Chlamydia tracomatis*, the padlock probe comprises a polynucleotide sequence selected from the group consisting of SEQ ID NO:8, SEQ ID NO:9, and SEQ ID NO:10; the primer comprises the polynucleotide sequence in SEQ ID NO:18; and the reporter probe comprises the polynucleotide sequence set forth in SEQ ID NO:11 or a polynucleotide corresponding to a region of SEQ ID NO:8.

In another aspect, the pathogen is *Chlamydia tracomatis* and the padlock probe hybridizes to a target region inside the cryptic plasmid DNA, for example, the 122-basepair or 140-basepair region within the cryptic plasmid targeted by the REALTIME CT/NG assay (Abbott Molecular, Des Plaines, Ill.), as described in Centers for Disease Control and Prevention, "Recommendations for the Laboratory-Based Detection of *Chlamydia trachomatis* and *Neisseria gonorrhoeae*." Recommendations and Reports 63, No. 2 (2014) and Gaydos et al., J. OM. Microbiol. 48(9): 3236-3243 (2010), incorporated herein by reference. In one aspect, two padlock probes, for example, to target both the 122-bp and 140-bp regions in the cryptic plasmid, are used.

In still another aspect, the pathogen is *Neisseria gonorrhoeae*, the padlock probe comprises a polynucleotide sequence selected from the group consisting of SEQ ID NO:14, SEQ ID NO:15, and SEQ ID NO:16; the primer comprises the polynucleotide sequence set forth in SEQ ID NO:18; and the reporter probe comprises the polynucleotide sequence set forth in SEQ ID NO:17 or a polynucleotide corresponding to a region of SEQ ID NO: 14. In one aspect, the pathogen is *Neisseria gonorrhoeae*, and the padlock probe hybridizes to a target region within the Opa gene or the M.NgoPII gene, such as a target region described in "Recommendations for the Laboratory-Based Detection of *Chlamydia trachomatis* and *Neisseria gonorrhoeae*," supra.

In another aspect, the pathogen is herpes simplex virus Type 1 or Type 2, and the padlock probe hybridizes to a target region within the glycoprotein B gene, for example, a target region described in Kim et al. J. Chn. Virol. 50: 26-30 (2012); Van Der Pol et al., J. Clin. Microbiol 50: 3466-3471 (2012); and Emmadi et al., J Mol Diagn 13: 583-604 (2011), incorporated herein by reference.

In one aspect, the pathogen is *Mycoplasma genitalium*, and the padlock probe hybridizes to a target region within the MG190 gene or the pdhD gene, for example, a target region described in McGowin et al., Infect. Immun. 80: 3842-3849 (2012) or Muller et al., J. Chn. Microbiol. 88:311-315 (2012), incorporated herein by reference.

In another aspect, the pathogen is *Trichomonas vaginalis* or *Gardnerella vaginalis*, and the padlock probe hybridizes to a target region within the 16S rRNA gene, for example, a target region described in Andrea et al., J. Clin. Microbiol. 49(3): 866-869 (2011); Cartwright et al., J. Clin. Biol. 50: 2321-2329 (2012); or Fredricks et al., J. Clin. Microbiol. 45: 3270-3276 (2007), incorporated herein by reference.

In still another aspect, the pathogen is a *Candida* species (e.g., *C. albicans* or *C glabrata*), and the padlock probe hybridizes to a target region on the internal transcribed spacer 2 (ITS2), for example, a target region described in Cartwright et al., J. Clin. Biol. 51: 3694-3699 (2013), incorporated herein by reference.

In various aspects, the kits and methods of the disclosure comprise a variant of a polynucleotide described herein, the variant having a nucleic acid sequence comprising at least 80%, at least 85%, at least 90%, at least 95%, or at least 98% sequence identity to any of the polynucleotides set forth in SEQ ID NOS: 1-21.

The following example is provided by way of illustration and is not intended to be limiting.

EXAMPLE

Design of HPV probe set for RCA product detection. A padlock probe was designed to include 5' and 3' target recognition sequences that, when hybridized to target HPV E6 mRNA, would bring the 5' and 3' ends of the padlock probe together for subsequent ligation. The extended sequence between the target-homologous regions of the RCA product provided a convenient hybridization site for the reporter probes. The reporter probe served as the positive control by accumulating at a control site downstream of the detection zone that was loaded with chitosan for non-specific capture of excess reporter probe. The reporter probe design included a primary amine at the 3' terminus for conjugation to N-hydroxysuccinimide (NHS)-functionalized reporter. Table 1 shows the synthetic oligonucleotides used for the HPV assay.

TABLE 1

| | |
|---|---|
| HPV E6 RNA target region analog | 84-TGCACCAAAAGAGAACTGCAATGT-107 (SEQ ID NO: 1) |
| Padlock for HPV | Full sequence:<br>pTCTTTTGGTGCATTTATTTCCTCAATGCTGCTGCTGTACTACTA GTGATTTACTTGGATGTCTACATTGCAGTTC (SEQ ID NO: 2)<br>5' end antisense to target: TCTTTTGGTGCA (SEQ ID NO: 3)<br>3' end antisense to target: ACATTGCAGTTC (SEQ ID NO: 4) |
| Reporter probe | TTTATTTCCTCAATGCTGCTGCTGTA (SEQ ID NO: 5) |
| Primer | AGCAGCAGCATTGAGGAAAT (SEQ ID NO: 6) |

All sequences are written 5'-3'.

Additional oligonucleotides suitable for an HPV assay include (written 5'-3') the primer TGCTGCCGGTCACTTAACAT (SEQ ID NO: 19), the padlock pCATCTGAAAAAATTTTTATGTTAAGTGACCGGCAGCATTTTTTCTAATCTGAAGCTT GGTGGACTCTTTTTTTCACTAGGCAGCC (SEQ ID NO: 20), and the HPV type 16 gap primer pAAAGAGA (SEQ ID NO: 21).

Reporter conjugation strategy. For optimal visualization and contrast on the white paper platform, paramagnetic microbeads were chosen as the visual reporter. By purchasing microbeads that were pre-functionalized with N-hydroxysuccinimide (NHS), the reporter probes and microbeads were covalently linked without additional reagents. Unreacted probe was recovered via magnetic isolation of the nanoparticles. Conjugation of the microbeads was performed according to the manufacturer's protocol. Briefly, 300 pL of 10 mg/mL of magnetic microbeads (1 pm average; Thermo Fisher Pierce, Rockford, Ill.) was transferred to a 1.5 mL Eppendorf tube and magnetically isolated. Following removal of the storage medium, the beads were resuspended in 1 mL of 1 mM HCl in Milli-Q water and vortexed gently for 15 seconds. Following magnetic isolation, the supernatant was removed prior to adding approximately 100 nmoles of aminated reporter probe suspended in a 300 pL aliquot of 50 mM borate, pH 8.5. The reaction was allowed to proceed for 2 hours to 3 hours at room temperature prior to magnetic isolation of the beads and removal of the supernatant. The beads were then resuspended in 1 mL of 100 mM glycine pH 2.0 and gently vortexed for 15 seconds. This step was repeated 3 times prior to rinsing the beads with Milli-Q water using the same methodology. Beads were then stored in Milli-Q water for subsequent use.

RCA of synthetic HPV E6 mRNA. The typically separate ligation and polymerization steps were combined into a single reaction. The 10×129 polymerase buffer was eliminated, and instead, 5 pL of 10× T4 ligase buffer (1 M Tris-Cl, 100 mM magnesium chloride, 50 mM ammonium sulfate, 10 mM ATP, pH 7.4) was combined with 400 units of T4 ligase, 160 pM padlock probe, 80 pM synthetic HPV target mRNA, 200 pM each dNTPs, 240 pM primer, 20 pg bovine serum albumin, 10 units of 129 DNA polymerase, and 50 pg of reporter probe-functionalized microbeads to a total volume of 50 pL using sterile Milli-Q water containing 0.1% (v/v) diethyl pyrocarbonate (DEPC). The final 1× reaction buffer comprised 100 mM Tris-Cl, 10 mM magnesium chloride, 5 mM ammonium sulfate, 1 mM ATP, pH 7.4, in 20% v/v methanol. The RCA reaction was then allowed to proceed for one hour at 30° C. Large-scale amplification of synthetic HPV E6 mRNA from concentrations as low as 600 pM and detectable amplification after only 30 minutes were also achieved.

Detection of RCA product on paper strips. For visual indication of product, magnetic microbeads were chosen due to their intrinsically dark-brown coloration. The microbeads were conjugated to a reporter probe antisense to the RCA product in order to provide high-contrast resolution against the white background of the Whatman #1 filter paper strips. Due to the large size of the RCA product, the 11 micron particle retention of the Whatman #1 filter paper retarded the product fairly quickly after initial wicking. The microbead/product complex formed a distinct band approximately 5 mm from the bottom of the paper strip due simply to size exclusion of the large product DNA strand within the porous paper (FIG. 2A). A positive assay control band was also included and consisted of a narrow band of immobilized chitosan applied 10 mm above the bottom of the strip. By including the functionalized microbeads in the RCA mixture, hybridization occurred during the amplification phase for immediate product visualization upon introduction of the paper strip. The upper chitosan band captured remaining functionalized microbeads due to non-specific adsorption of DNA to indicate that the test worked appropriately.

*Chlamydia trachomatis.* The design strategy and protocol described above for HPV was also used to develop an assay for detecting polynucleotides from the pathogen *Chlamydia trachomatis*. Table 2 shows the synthetic oligonucleotides used for the *Chlamydia* assay.

TABLE 2

| | |
|---|---|
| C. trachomatis 16S rRNA target region analog | 79-ACGATTGTTTAGTGGCGGA-98 (SEQ ID NO: 7) |
| Padlock Probe for Chlamydia | Full sequence: pAACAATCGTTTTATTTCCTCAATGCTGCTGCTGTACTACTAGTG ATTTACTTGGGATGTCTTCCGCCACTA (SEQ ID NO: 8) 5 region antisense to target: AACAATCGT (SEQ ID NO: 9) 3' region antisense to target: TCCGCCACTA (SEQ ID NO: 10) |
| Reporter probe | TTTATTTCCTCAATGCTGCTGCTGTA (SEQ ID NO: 11) |
| Primer | AGCAGCAGCATTGAGGAAAT (SEQ ID NO: 12) |

All sequences are written 5'-3'.

*Neisseria gonorrhoeae* assay. The design strategy and protocol described above for HPV was used to develop an assay for detecting gonorrhea. Table 3 shows the synthetic oligonucleotides used for the gonorrhea assay.

TABLE 3

| | |
|---|---|
| N. gonorrhoeae 16S RNA target region analog | 560-ACTGCGTTCTGAACTGGGTG-774 (SEQ ID NO: 13) |
| Padlock Probe for N. gonorrhoeae | Full sequence: pAGAACGCAGTTTTATTTCCTCAATGCTGCTGCTGTACTACTAG TGATTTACT TGGATGTCTCACCCAGTTC (SEQ ID NO: 14) 5'end antisense to target: AGAACGCAGT (SEQ ID NO: 15) 3'end antisense to target: CACCCAGTTC (SEQ ID NO: 16) |

TABLE 3-continued

```
Reporter probe   TTTATTTCCTCAATGCTGCTGCTGTA (SEQ ID NO: 17)

Primer           AGCAGCAGCATTGAGGAAAT (SEQ ID NO: 18)
```

All sequences are written 5'-3'.

The foregoing Example demonstrates that the kits and methods described herein allow for rapid and portable detection of a pathogen in a biological sample without the use of laboratory instrumentation. The design strategy and protocol provided above is applicable to other pathogens of interest including, but not limited to, the pathogens described herein.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed:

1. A kit for detection of a pathogen polynucleotide in a biological sample
comprising:
(a) a reaction vessel comprising: (1) a padlock probe comprising a 5' end complementary to a first section of the pathogen polynucleotide and a 3' end complementary to a second section of the pathogen polynucleotide, wherein the first section and second section of the pathogen polynucleotide sequence are located adjacent to each other; (2) a ligase that anneals the 5' and 3' ends of the padlock probe together to form a circular padlock probe; (3) a primer comprising a polynucleotide complementary to a portion of the padlock probe; (4) a polymerase; and (5) a reporter probe;
(b) a reaction buffer comprising Tris-Cl, magnesium chloride, ammonium sulfate, ATP, and methanol; and
(c) a test strip.

2. The kit of claim 1, wherein the pathogen is selected from the group consisting of human papillomavirus, *Chlamydia tracomatis*, and *Neisseria gonorrhoeae*.

3. The kit of claim 1, wherein the padlock probe comprises a polynucleotide sequence selected from the group consisting of SEQ ID NO:2, SEQ ID NO:3, SEQ ID NO:4, SEQ ID NO:8, SEQ ID NO:9, SEQ ID NO:10, SEQ ID NO:14, SEQ ID NO:15, SEQ ID NO:16, and SEQ ID NO:20, and a variant having at least 90% sequence identity to SEQ ID NO:2, SEQ ID NO:3, SEQ ID NO:4, SEQ ID NO:8, SEQ ID NO:9, SEQ ID NO:10, SEQ ID NO:14, SEQ ID NO:15, SEQ ID NO:16, or SEQ ID NO:20.

4. The kit of claim 1, wherein the padlock probe comprises the polynucleotide sequences of SEQ ID NO:3 and SEQ ID NO:4, SEQ ID NO:9 and SEQ ID NO:10, SEQ ID NO:15 and SEQ ID NO:16, or variants having at least 90% sequence identity to SEQ ID NOS: 3 and 4, SEQ ID NOS: 9 and 10, or SEQ ID NOs: 15 and 16.

5. The kit of claim 1, wherein the padlock probe comprises the polynucleotide sequence of SEQ ID NO:2, SEQ ID NO: 8, SEQ ID NO:14, SEQ ID NO:20, or a variant having at least 90% sequence identity to SEQ ID NO: 2, SEQ ID NO: 8, SEQ ID NO: 14 or SEQ ID NO: 20.

6. The kit of claim 1, wherein the ligase is T4 DNA ligase.

7. The kit of claim 1, wherein the primer comprises the polynucleotide sequence of SEQ ID NO:6, SEQ ID NO:12, SEQ ID NO:18, SEQ ID NO:19, SEQ ID NO:21, or a variant having at least 90% sequence identity to SEQ ID NO: 6, SEQ ID NO: 12, SEQ ID NO: 18, SEQ ID NO: 19, or SEQ ID NO: 21.

8. The kit of claim 1, wherein the polymerase is φ129 polymerase or Bst DNA polymerase.

9. The kit of claim 1, wherein the reporter probe comprises a polynucleotide sequence (a) selected from the group consisting of SEQ ID NO:5, SEQ ID NO:11, SEQ ID NO:17, and a variant having at least 90% sequence identity to any of SEQ ID NO: 5, SEQ ID NO: 11 or SEQ ID NO: 17 or (b) corresponding to a region of SEQ ID NO:2, SEQ ID NO:8, SEQ ID NO:14, or SEQ ID NO:20.

10. The kit of claim 1, wherein the reporter probe comprises a polynucleotide sequence identical to the polynucleotide sequence of the padlock probe adjacent to the 5' complementary end.

11. The kit of claim 1, wherein the reporter probe is conjugated to a microparticle.

12. The kit of claim 11, wherein the microparticle has a diameter less than about one micrometer.

13. The kit of claim 11, wherein the microparticle is a nylon microparticle, a gold microparticle, or a magnetic microparticle.

14. The kit of claim 1, wherein the reaction buffer comprises about 100 mM Tris-Cl, about 10 mM magnesium chloride, about 5 mM ammonium sulfate, about 1 mM ATP, pH about 7.4, in about 20% v/v methanol.

15. The kit of claim 1, wherein the reaction buffer comprises about 50 mM Tris-Cl, about 10 mM magnesium chloride, about 10 mM ammonium sulfate, about 4 mM DTT, pH about 7.5, and about 0.1 mM to about 1 mM ATP.

16. The kit of claim 1, wherein the test strip comprises filter paper, optionally filter paper comprising a pore size of about 11 micrometers.

17. The kit of claim 1, wherein the test strip comprises chitosan.

18. The kit of claim 1, wherein the pathogen is
(a) human papillomavirus; the padlock probe comprises a polynucleotide sequence selected from the group consisting of SEQ ID NO:2, SEQ ID NO:3, SEQ ID NO:4, SEQ ID NO:20, and a variant having at least 90% sequence identity to any of SEQ ID NO: 2, SEQ ID NO: 3, SEQ ID NO: 4 or SEQ ID NO: 20; the primer comprises the polynucleotide sequence of SEQ ID NO: 6, SEQ ID NO:19, SEQ ID NO:21, or a variant having at least 90% sequence identity to SEQ ID NO:6, SEQ ID NO:19, or SEQ ID NO:21; and the reporter probe comprises the polynucleotide sequence of SEQ ID NO: 5 or a variant having at least 90% sequence identity to SEQ ID NO:5, -or a polynucleotide corresponding to a region of SEQ ID NO:2 or SEQ ID NO:20;
(b) *Chlamydia trachomatis*; the padlock probe comprises a polynucleotide sequence selected from the group consisting of SEQ ID NO:8, SEQ ID NO:9, SEQ ID NO:10, and a variant having at least 90% sequence identity to SEQ ID NO: 8, SEQ ID NO: 9, SEQ ID NO: 10; the primer comprises the polynucleotide sequence of SEQ ID NO: 12 or a variant having at least 90% sequence identity to SEQ ID NO:12, and the reporter probe comprises the polynucleotide sequence of SEQ ID NO:11 or a variant having at least 90% sequence identity to SEQ ID NO:11, or a polynucleotide corresponding to a region of SEQ ID NO:8; or
(c) *Neisseria gonorrhoeae*; the padlock probe comprises a polynucleotide sequence selected from the group consisting of SEQ ID NO:14, SEQ ID NO:15, SEQ ID NO:16, and a variant having at least 90% sequence identity to SEQ ID NO: 14, SEQ ID NO: 15 or SEQ ID NO: 16; the primer comprises the polynucleotide sequence of SEQ ID NO:18 or a variant having at least 90% sequence identity to SEQ ID NO:18, and the reporter probe comprises the polynucleotide sequence of SEQ ID NO:17 or a variant having at least 90% sequence identity to SEQ ID NO:17, or a polynucleotide corresponding to a region of SEQ ID NO:14.

* * * * *